United States Patent
Lindmayer

(10) Patent No.: US 7,749,187 B2
(45) Date of Patent: Jul. 6, 2010

(54) NEEDLELESS INJECTION DEVICE AND CARTRIDGES

(76) Inventor: István Lindmayer, str Homokhegy No. 12, Döbrököz H-7228 (HU)

(*) Notice: Subject to any disclaimer, the term of this patent is extended or adjusted under 35 U.S.C. 154(b) by 89 days.

(21) Appl. No.: 10/568,781

(22) PCT Filed: Aug. 11, 2004

(86) PCT No.: PCT/HU2004/000083
§ 371 (c)(1), (2), (4) Date: Feb. 21, 2006

(87) PCT Pub. No.: WO2005/018720
PCT Pub. Date: Mar. 3, 2005

(65) Prior Publication Data
US 2006/0270972 A1 Nov. 30, 2006

(30) Foreign Application Priority Data
Aug. 21, 2003 (HU) .................. 0302704

(51) Int. Cl.
*A61M 5/30* (2006.01)
(52) U.S. Cl. ............ 604/68; 604/72; 604/134; 604/138; 604/183; 604/187; 604/197; 604/218; 604/235
(58) Field of Classification Search ............ 604/68–70, 604/72, 110, 134, 135–136, 138, 181, 183, 604/187, 188, 193, 197, 198, 218, 235; 128/919
See application file for complete search history.

(56) References Cited
U.S. PATENT DOCUMENTS

| | | | | |
|---|---|---|---|---|
| 4,596,556 A | * | 6/1986 | Morrow et al. | 604/70 |
| 4,623,332 A | * | 11/1986 | Lindmayer et al. | 604/68 |
| 4,722,728 A | * | 2/1988 | Dixon | 604/68 |
| 5,599,302 A | * | 2/1997 | Lilley et al. | 604/68 |
| 5,695,472 A | * | 12/1997 | Wyrick | 604/136 |
| 5,800,388 A | * | 9/1998 | Schiff et al. | 604/68 |
| 7,473,241 B2 | * | 1/2009 | Hjertman et al. | 604/68 |
| 2001/0031945 A1 | * | 10/2001 | Haar et al. | 604/68 |
| 2002/0055712 A1 | | 5/2002 | Neracher | |
| 2003/0065286 A1 | * | 4/2003 | Landau | 604/69 |

FOREIGN PATENT DOCUMENTS

| GB | 681 098 A | 10/1952 |
|---|---|---|
| WO | WO-03/000319 A | 1/2003 |
| WO | WO-03/066143 A | 8/2003 |

* cited by examiner

*Primary Examiner*—Nicholas D Lucchesi
*Assistant Examiner*—Quynh-Nhu H Vu
(74) *Attorney, Agent, or Firm*—Birch, Stewart, Kolasch & Birch, LLP

(57) ABSTRACT

A needleless injection device with a lower part receiving the agent cartridge and an upper part providing the energy needed for injection. The upper part contains energy store units capable of elastic form-change. Rotating the lower part in relation to the upper part causes the lower part to move along the longitudinal axis toward the upper part, resulting in the tension state of the energy storage structural elements. Furthermore, the device has a lock maintaining the tension of the energy storage units and component to release the lock. Among the energy storage structural parts there is at least one start unit capable of storing at least 60% of the total discharge energy (pressure), with the reversible elastic distortion not exceeding 25% of the internal length of the agent cartridge. The device has separate structural components for stretching the start unit and limiting its relaxation.

14 Claims, 2 Drawing Sheets

NEEDLELESS INJECTION DEVICE AND CARTRIDGES

BACKGROUND OF THE INVENTION

1. Field of the Invention

The invention relates to a needleless injection device with a lower part receiving an agent cartridge and an upper part providing the energy needed for injection; the upper part contains energy store units, namely start unit(s) and supplementary unit(s), capable of elastic form-change; furthermore, the device has a lock maintaining the tension of the energy store units and components to release the lock; and the invention also relates the agent cartridge.

2. Description of Related Art

An advantage of the needleless solutions is that no infection is possible through multiple use of needles or defective sterilization. Another advantage is that agent injection with a needleless device causes a twenty times smaller fracture (an injection hole of cc. 0.008 mm$^2$) on the epidermis than the smallest needle ever used before. Consequently, the needleless solution causes the patient less pain. The agent is prepared in a sterile cartridge, which precisely fits into the injection device. The thrust needed for the injection of the agent is supplied by the expansion of compressed gas as in U.S. Pat. No. 4,913,699, or a mechanical spring structure as used in U.S. Pat. No. 5,190,523. Also known is a solution in which the injection energy is given by the explosion of a suitable detonating charge. The known needleless injection devices usually comprise two parts. One serves for receiving the agent cartridge, while the other is the energy storage unit, where the spring, the compressed gas container, or the explosive capsule is situated. These devices are operated in a way that in the case of a spring, the spring is flexed, and locked in this position. The agent cartridge is inserted, which also contains the piston to discharge the agent. Then the device is positioned on the skin surface with the discharge hole down, and release the energy stored in the energy storage unit. If it works with a spring, the lock is released, in other solutions, the gas capsule is opened, or the explosive is detonated. In each case the released energy thrusts the piston powerfully forwards, and injects the agent stored in the cartridge into the skin, or through the skin into the hypodermic tissues or the muscles. As is known, giving a traditional injection, the doctor thrusts the needle into the desired point with rapid movement, thus opening the way in for the agent. Then, with a moderate push of the syringe, they cause a relatively slow influx of the agent, otherwise the process would be painful and would cause further fraction in the tissues. In injecting the agent, the needleless injection device is expected to perform the same task as expected from a doctor or a nurse in the manual process. To achieve the desired result, the device must be easy to use, that is to say, if it is a spring, it must be easy to flex, it must store sufficient energy, and deliver its energy at a sufficient speed. The injection should not be painful and should cause minimal fraction in the tissues. For the desired spread of this up-to-date device it is indispensable that the device be available for users, including health security institutions, in appropriate quality and at an affordable price. In the case most of the known devices these requirements are not always met completely. The devices, available in patents mentioned above and other marketed products, contain energy storing units capable of injecting agents into the skin, under the skin, into muscles at the requisite speed, but the initiating step of punching the skin, that is corresponding to thrusting the needle with the classic process, is achieved in a way that on releasing, the energy impulse causes a hit-like impact on the piston of the agent cartridge. We know this solution from the specification of WO 03/000319. The released energy first accelerates the piston rod of the energy storing unit, which reaches the cartridge piston with a collision, and only after the collision does the continuous push of the piston begin. The impact exerted by the piston rod of the energy storage unit on the agent cartridge piston will be passed on to the body surface in contact with the device and there causes injuries, suffusion, discoloring and consequent pains.

Some solutions experience with combined spring structure. Although they cannot eliminate the impact on the body, but attempt to achieve certain shock absorption to diminish impact originated injuries, as known from U.S. Pat. No. 4,722,728.

These are based on the concept that the group of springs, as all springs if metal, starts off with a high initial energy, which gradually echoes off. At the moment of dislocking, it produces the impact punching the epidermis, then it empties the agent storage space with linearly decreasing energy, into the body. However, the harmful impact cannot be eliminated with this solution, and it fails to eliminate the described shock absorption effectively. The solution of WO 03/066143 uses also two springs, but they and their effect is not separated one from other. The Patent Specification U.K. 681,098 gives a solution to eliminate most of these problems. It uses a two-stage jet with a hard spring start unit, and separated from it a soft spring for the following injection. For compressing the springs the device is provided with a pull rod, what they have to pull along the long axis of the device with the help of the knob on the top of it. The development efforts are orientated towards an energy storage and release structure which is enabled to store optimal amount of energy and to release it always at the optimal time and speed suitable for fulfilling the task. Too low impact is unsuitable since it causes a partial or complete failure to inject the agent. Perhaps due to a loss or too low a level of energy, the cartridge is not emptied entirely. One of the most important parts of the device is the discharge hole, the precise measure and ideal profile cannot be satisfactorily produced from glass or metal. Thus, for discharge holes, glass cartridges receive metal inlays, metal cartridges receive glass or semiprecious stones (e.g. sapphire or ruby) inlays, the fitting of which into the cartridge raises solidity, while inside the cartridge, owing to turbulences in the joining and contact zones of the metal and the glass, hydrodynamic problems. Although the devices known from patents and available on the market meet the elementary health and technical requirements, they cannot manage the above described quality services. They are also unable to provide the affordable sales price acceptable with disposable devices.

SUMMARY OF THE INVENTION

The goal of the invention is the development of a needleless injection device with an agent cartridge eliminating the abovementioned drawbacks, on a reliable technical level, using simple production technology and a more favorable, economical price standard, facilitating disposability.

The invention is based on the recognition that the injection of the agent in/under the skin or in the muscles can be carried out without an impact if the energy released in the first few tenth seconds has enough power to thrust the entry channel through the epidermis immediately. In such a solution the piston in the agent cartridge is in continuous contact with the piston rod transferring the energy, and, unlike the known structures, it is not necessary that the piston rod be first accelerated by the released energy, and use this speed to blow into the agent cartridge piston.

The described recognition also includes the innovative idea that at least 60% but optimally 80-90% of the released energy should fall on the first 15-20% section of the whole distance the piston takes. According to the invention, this requirement can be realized with a complex spring structure, in which one component transfers significant energy with a short relaxing movement, while the other component(s) cut out the unit providing the initial high energy, and ensure the run of the piston in the cartridge right as far as the discharge hole at the appropriate moderate speed. Consequently, the spring structure of the invention should comprise a "hard" component with high energy storage capacity at a relatively small change in size and a unit of comparatively softer other component(s).

In contrast with the solution with an energy storage unit comprising several different springs, but still requiring an impact at the launch of the piston, we realized that a variety of springs is only effective and transfers the necessary time characteristics of energy transfer, which is capable of fulfilling the task without an impact if at the time of launch, the mentioned "hard" start unit of the energy storage structure is integral with the low-energy (soft) spring, but after the 15-20% movement of the piston it becomes separate and independent from the other supplementary units both in the tense (energy storing) and the relaxing period of operation. The invention contains a further recognition that it is not enough to select and fit the springs, but they should be applied only in the stage of linear movement where the stress does not cause permanent distortion. This makes it necessary to fit the device with separate structural units limiting the tension and the relaxation of the starter and supplementary energy storage units respectively.

The practical result of our recognition is the possibility of avoiding to use expensive cartridges produced from glass or metal, for which a separate discharge hole inlays would be necessary, as agent outlet. Instead of it we may use well the chemical stabile and easy produce cartridge of plastic, which due to conical seat provides satisfactory stability already with 0.5-0.8 mm wall thickness and we may manufacture with high precision the discharge hole from the cartridge's own material.

Thus the agent cartridge according to the present invention may successfully and economically produced of plastic, since it will be used only once, and after our inventive recognition we may produce the discharge hole from the own material of cartridge consider its size, profile and precision equal with the metal discharge hole. This solution has the advantage that there is no any break-line on the inner surface of the cartridge because there are no two different material adjoining one with other. Thus we may avoid the turbulence of liquid stream, and achieve an energy spare, consequently smaller size and price of the device. Further we may also avoid the danger of disengagement of the inlay, and the price of the cartridge is essentially lower than of the variant produced with metal inlay discharge hole.

The inventive solution based on the said recognition is a needleless injection device with a lower part receiving an agent cartridge and an upper part providing the energy needed for injection; the upper part contains energy store units, namely start unit(s) and supplementary unit(s), capable of elastic form-change; furthermore, the device has a lock maintaining the tension of the energy store units and components to release the lock.

The device may be characterized in that a long tube section of the lower part, with external thread stretches into the upper part and at the bottom fits into the short internal thread of the adjoining part of the upper part, thus the lower part is attached to the upper part revolving manner, moving in a telescopic way, and results the tension state of the energy store units; at least one start unit, capable of storing min. 60%, preferably 80-90% of the total discharge energy (pressure), with the reversible elastic distortion at max. 25%, practically 15-20% of the internal length of the agent cartridge; wherein the start unit is a bundle of polyurethane springs fitted inside the device in a separate case, at stretching it is joined with the mean transferring the stretching power, preferably with the lock mechanism, by a spacer, having no contact with other energy store units, namely with supplementary unit(s).

The device preferably may be characterized in that the supplementary unit(s) are volute springs, comprising 2-8, preferably 4-5 volute springs fitted coaxially in each other, surrounding the geometric axis of the upper part, or using more supplementary units, these are positioned symmetrically around the geometric axis.

The device preferably may even be characterized in that practically the release mechanism is a release button situated at the top of the upper part, attached to a release rod reaching down to the lock mechanism in the axis of the upper part. Preferably the device may also characterized by that the discharge hole of the cartridge's is manufactured from the cartridge's own material.

The device may be characterized in that the discharge hole of the agent cartridge is situated precisely in the axis of symmetry of the cartridge.

BRIEF DESCRIPTION OF THE DRAWINGS

The invention is described in details in production samples based on the attached drawings, which, however, do not limit the applicability of the invention or the requested protection range on the production samples.

DETAILED DESCRIPTION OF THE INVENTION

Figures 1, 2, 3:
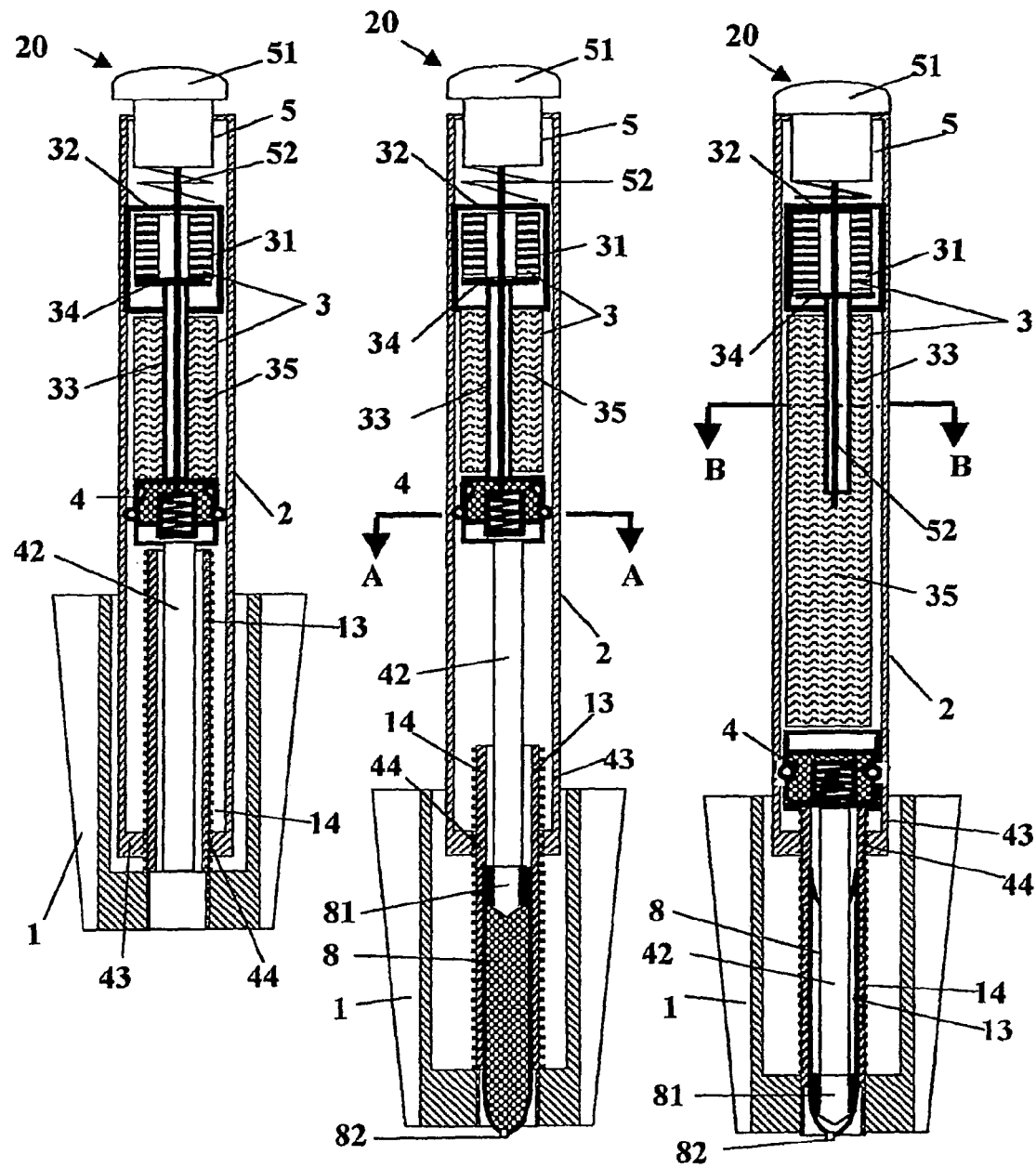
FIG. 1. The invented device in longitudinal section is telescopically locked (pre-stressed) position, without a cartridge.
FIG. 2. The device in longitudinal section, in telescopically open position, loaded with full agent cartridge.
FIG. 3. The device in longitudinal section, in telescopically open (relaxed) position, containing the emptied cartridge.
Figure 6:
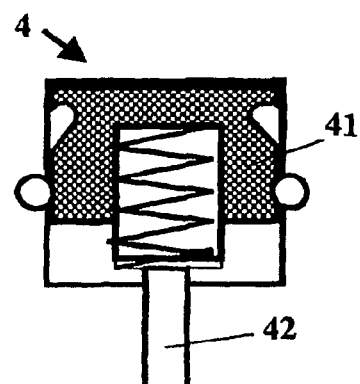
FIG. 6. The sketch of the lock mechanism of the device in locked position.
Figure 7:
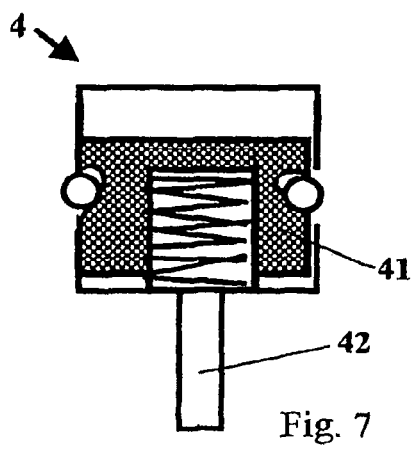
FIG. 7. The sketch of the lock mechanism of the device in released position.
Figure 8:
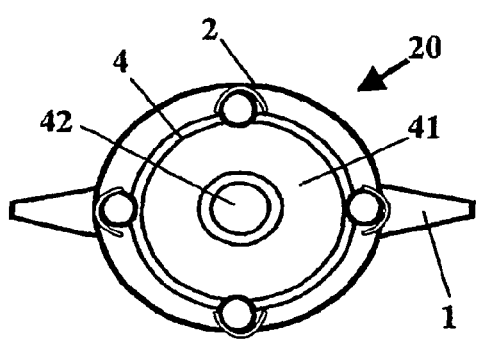
FIG. 8. The device in cross-section according to the A-A section of FIG. 2.

The needleless injection device 20 is basically a cylindrical tube comprising an upper part 2 and an adjoining lower part 1, where the terms "upper" and "lower" apply on the parts farther and nearer to the end of the device 20 which contacts the epidermis during injection (FIG. 1.). The upper part 2 contains the following parts from up downwards: releasing mechanism 5, energy storage parts 3, lock mechanism 4 and the internally threaded part 43 adjoining to the lower part 1. The lower part 1 is such an integral unit, the central part of which is a tube stretching into the upper part 2, and its external part, integral with the latter, surrounds the adjoining part 43 of the upper part 2 as a case. The tube 13 of the lower part 1, which stretches into the upper part 2, has an external thread 14, that fits into the internal thread 44 ensuring the contact. On the external surface of the lower part 1 there are wings to provide easy grip when turning the lower part 1. The mentioned adjoining part 43 of the upper part 2 is a hollow case, which narrows down to the size of the tube 13 of the lower part 1 only at the bottom, where there is a sufficient number of internal threads 44. The number of internal threads is just enough to hold the internally threaded tube 13 of the lower part 1 safely. On turning the lower part 1, the tube 13, clutching the internal thread 44 of the adjoining part 43 of the upper part 2 penetrates into the upper part 2, while the external part slips upon it (FIG. 1). When turned reversely, it withdraws (FIG. 2). In such a way, clasped on each other with threads, the lower part 1 and upper part 2 move into each other and open up in a telescopic way. Inside the adjoining part 43 of the upper part 2 is the lock mechanism 4 (FIG. 6). The lock mechanism 4 is a closed cylindrical springy cup 41 precisely fitting into the upper part 2, in which a socket moves like a piston, pushed by a locking spring towards the cover of the springy cup 41. On the cylindrical surface of the socket, distributed uniformly around, there are three or four pockets, and in the cylindrical wall of the springy cup there is an equal number of perforations distributed in a circulate fashion. In every pocket and overlapping perforation there is a locking ball. When the locking spring is in tension, the pockets of the socket are overlapping the perforations of the springy cup 41. Since the locking spring pushes the socket upwards, the pockets of the socket, optimally shaped with an evolvent profile, press the locking balls on the internal surface of the upper part 2, but the balls prevent the socket from moving up to the top of the springy cup 41. When the springy cup 41 moves upwards inside the adjoining part 43 of the upper part 2, it reaches a cross section, where on the inside surface of the upper part 2, there is an equal number and distribution of locking pockets as in the springy cup 41 (FIG. 8). As soon as the springy cup 41 arrives there, the locking balls spring into the pockets, which stops the free movement of the springy cup 41. The locking spring pushes the socket against the top of the springy cup, which stops the balls from leaving the pockets. This holds the springy cup 41 in position (FIG. 7). To the locking bottom cover of the spring cup 41 a piston rod 42 is fixed in rigid contact. The piston rod 42 is situated precisely in the longitudinal axis of the device 20. The agent to be injected is in a separate cartridge 8. The size and shape of the cartridge 8 is exactly and jointlessly fitting into the tube 13 of the lower part 1 (FIG. 2). After inserting the cartridge 8, the lower part 1 is closeable with a screwable cover. It is more practical, however, to fit the cartridge 8 with a threaded surface part, which fits into the thread formed at the bottom of the lower part 1. On the lower, threaded part of the cartridge 8 is the discharge hole 82 for the injection of the agent. Inside the cartridge 8 there is a piston 81. The interior part of the cartridge 8 is a precise cylinder, in which the piston 81 is allowed to move freely but providing perfect tightness everywhere. The piston rod joining to the bottom cover of the springy cup lock is such in length that in the locked position of the lock mechanism 4, the piston rod 42 reaching into the tube 13 of the lower part 1 precisely touches the piston 81 of the full cartridge 8.

In the upper part 2 of the device 20, above the lock mechanism 4, the energy storage parts 3 are situated. Higher up, that is under the release mechanism 5, is the energy storage start unit 31, which, with the supplementary unit 35, is responsible for punching the epidermis and develop a transfer channel in order to inject the agent. To solve the problem, only a small amount of agent should be used, but with a powerful shot at the skin. Consequently only a very short, but extremely rapid movement is allowed for the piston in the cartridge 8.

Figure 4:
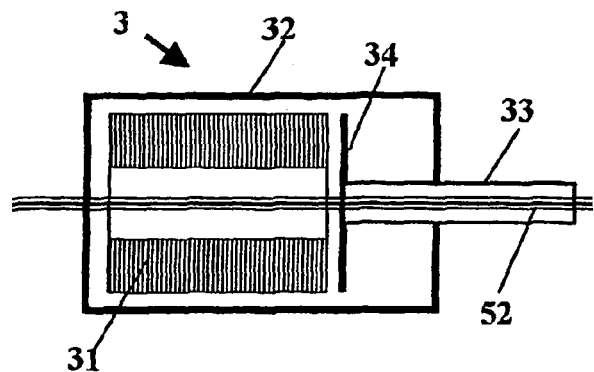
FIG. 4. The sketch of the start unit in pre-stressed position.
Figure 5:
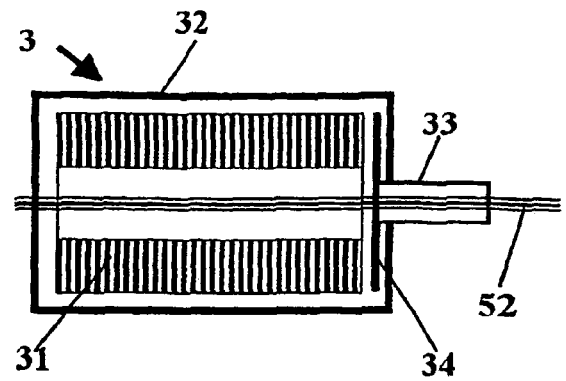
FIG. 5. The start unit of the device in relaxed position.
Figure 9:
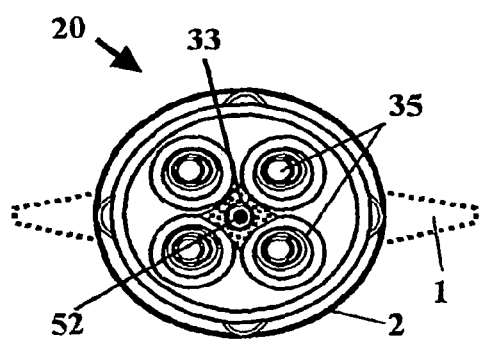
FIG. 9. The cross-section of the device according to the B-B section of FIG. 3.

In the present production sample therefore the start unit 31 is a polyurethane spring closed in a case 32 (FIG. 4). The case 32 is fastened to the upper part 2, thus the case 32 cannot move in it. To the top of the case is supported by the start unit 31, while its bottom cover is perforated in the axis of the device 20, and a spacer 33 is led through the perforation. The spacer 33 is a sufficiently hard, heavy-duty and non-flexible profiled solid with a unified interior longitudinal channel, situated in the axis of the device 20. The upper end of the spacer 33 is fixed to a start stay 34 plate, which can move in the 32 socket towards the axis of the device 20 (FIG. 5). The start stay 34 plate presses against the bottom of the start unit 31. In the interior of the upper part 2 under the 32 socket there are more energy storage supplementary units 35. Each supplementary unit 35 consist of several, optimally 4-6 volute springs, inserted into each other coaxially. The 3-5 identical supplementary units 35 surround the axis of the device 20 and the spacer 33 cover in equal distribution. The profile of the spacer has as many concave elliptic grooves running around the outside surface as the number of supplementary units around (FIG. 9). The ribs between the concave surfaces also serve as stiffeners. Another possible version is where there is only one supplementary unit 35 and the spacer 33 stands in the common center of the coaxial volute springs. According to the experience, this solution provides a more limited possibility of regulation in terms of a practical selection and combination of the springs. The possible movement limits of the springy cup 41 in the adjoining part 43 of the upper part 2 go from near the internally threaded 44 bottom part of the adjoining part 43 as far as the locked position of the springy cup 41. The difference between these two extreme positions of the springy cup 41 (more exactly the two positions of the cover of the springy cup 41) define the space the tension and relaxed position of the energy storing supplementary units 35 can use inside the upper part 2 (FIGS. 2 and 3). To select the length of the spacer 33 one has to define to what extent that is how many millimeters the start unit 31 in the case 32 has to be pressed for the tension. The length of the spacer has to be selected so that it be lifted by the springy cup 41 this much before reaching the locked position, that is, reach in so much deeper than the locked end position of the springy cup 41. The release mechanism 5 is responsible for ceasing the locked position and releasing the stored energy. The releasing mechanism 5 is at the top of the upper part 2. It is a release button 51, which can be pressed against a mild safety spring, and an adjoining release rod. For the release rod 52 there is a channel as far as the socket in the springy cup 41. At the top of the case 32 and the cover of the springy cup 41, there are perforations. The release rod 52 goes along these and the centre of the ring-shaped start unit 31 and the hole in the spacer 33. On pressing the release button 51, the socket is pressed down as far as the locking balls, which thus progress from the locking pockets to the socket pockets, which ceases the locked position. The release button 51 is surrounded with a hard protective collar to prevent unintended pressure. According to another solution, a 30-60° turn of the release button 51 in either direction is blocked by a stop, which prevents the button from pressing.

The operation and application of the device is as follows: The unloaded device 20 is prepared for operation. The empty cartridge 8 of the last injection has been removed from the lower part 1, but then the piston rod 42 is still in the tube 13 of the lower part 1, and the bottom of the springy cup 41 is seated on the tube 13 of the lower part 1 (FIG. 1). The lower part 1 is now grasped at the wings and screwed into the upper part 2. By doing so, the springy cup 41 in the adjoining part 43 is gradually lifted up to the cross section of the lock. Further lifting is impossible because the wings of the lower part 1 are stopped by the edge formed on the external surface of the upper part 2. By lifting the springy cup 41, the energy storing supplementary units 35 are brought from relaxed position into tension, and in the last phase of the process, the start unit 31 is also flexed with the mediation of the spacer 33 and the starter stay plate 34. By turning the lower part 1 manual energy is transferred to the device 20, which stores it in the energy storage structural parts 3. When the springy cup 41 reaches the locked position, the energy storing role of the lower part 1 ceases. This role is taken over by the lock mechanism 4 because the lock balls bear the pressure against the tense springs. Next, by turning the lower part 1 reversely, opening up in a telescopic way, the tube 13 withdraws from the hollow of the adjoining part 43, leaving the piston rod 42 behind (FIG. 2). This has emptied the tube 13 of the lower part 1, leaving the space for inserting the cartridge 8. The full cartridge 8 is inserted into the tube 13, with the discharge hole 82 outwards (that is downwards), and screwed into the cartridge reception threads. Due to the precise measurement and the uniform size of cartridges 8 manufactured for the device 20, the piston 81 of the cartridge 8 screwed into the tube 13 precisely touches the bottom end of the piston rod. Then, positioning the device with the discharge hole against the treated body part, and unlocking with the releasing mechanism 5, the energy storage structure 3 press the springy cup 41 and the piston rod 42 powerfully towards the cartridge 8, where the piston 81 injects the agent through the discharge hole 82 into the required depth in the treated body part. The gist of the invention is understandable by a detailed analysis of the energy transfer process following the release. On releasing the lock, the start unit 31 and the supplementary units 35 break free from the blockade together, jointly producing the 600 bar pressure in the agent cartridge required for opening the injection channel. With this, the role of the powerful start unit 31 ends. Not because it has transferred all its energy, but because the starter stay plate 34 has reached the bottom of the case 32 and is physically blocked in further relaxing form change (FIG. 5). As a result of continuous downward movement, the cover of the springy cup 41 leaves the spacer 33. Thus, no more energy transfer is possible by the start unit 31. This structure and arrangement ensures that the start unit 31 can operate only on linear section, between 20-60% stretch rates, which is adequately designable and measurable. According to experience, a more powerful tension or relaxation of the springs would result in permanent distortion. Furthermore, it can be ensured that the power opening the injection channel should appear already in the first 0.2 sec., without an inconvenient acceleration of the injection. In our sample the full length of the cartridge 8 is 20 mm, out of which only 3-5 mm is necessary for opening the channel. Only the supplementary units 35 of likewise designed pressure continue work. With this solution, the progress and timing of the manual injection performed by a health professional can be almost perfectly monitored.

It is to be stressed that this invention fundamentally differs both in theory and practice from known solutions including known solutions applying combinations of different springs. Merely by the simultaneous use of springs of different characteristics, the task is not solved, because the start and following continuous stages are not appropriately separated in time. At these earlier versions the pressure of the start stage cannot be put high enough, because later it would interfere with the injection at a moderated speed. Thus, the impact on the piston cannot be missed in order to open the injection channel. This is fully eliminated in our solution. On the other hand, in earlier solutions, since at tension energy storing is done in the whole energy storage unit simultaneously, the produced energy cannot be differentiated in the complex system to the different energy storing components. At this invention, as obvious from the description and the plans, not only the measure and time of energy transfer are separated as regards the start unit 31 and the supplementary units 35, but also the energy-intake, the tension.

The device 20 according to this invention is optimally shaped if the tube 13 interior of the lower part 1 receiving the cartridge 8 be precisely fitting with the external shape of the cartridge 8. For this tube 13 interior of the lower part 1 is not of cylindrical shape but that of a truncated cone where the wider end of the truncated cone superfices is below, the narrower is above. The angular offset of the conoid as compared to the vertical, that is the geometric axis of the device 20, is 1.5°. The angular offset is selectable between 1.2 to 1.8°, the 1.5° is the rate in this sample. The superfices of the cartridge 8 is also of a truncated cone, the angular offset of which precisely fits the tube 13 interior cone, that is 1.5°. This shape, like the "Morse-cone", warrants the perfect bedding of the cartridge 8 inside the tube 13, over the whole contact surface. On launching the agent, an extremely high pressure affects the piston 81, next the agent and the bottom of the cartridge 8 and the area around the discharge hole. It is important that this pressure not be born by the threads fastening the cartridge 8 alone, but also the gripping and frictional force between the walls of the cartridge 8 and the interior of the lower part 1 tube 13. This necessitates an appropriately tight contact, which, according to experience, cannot be safely realized at fitting cylindrical surfaces. The outer part of the lower part 1 is manufactured from shock-proof plastic, the integral, externally threaded 14 tube 13 is from metal. At our product experiments prove that the plastic cartridge 8 manufactured with a wall thickness of 0.5-1 mm and a truncated cone fitting grips and blocks extremely tightly inside the tube 13 of the lower part 1.

The cartridge 8 can be manufactured from any plastic with a sanitary certificate which is applicable for die-cast processes. Usually thermoplastic materials are used like polycarbonates, polypropylenes, or polyethylene. The device 20 is for multiple use, while the cartridge 8 for only one. It is important in the practical use of the invention that the cartridge 8 is a material-saving and cheap product. The cartridge of this invention is optimally manufactured from thermoplastic, with a die-cast technology and a wall thickness of 1 mm. Also the discharge hole is formed during the die-cast process. In the ready-made cartridge 8 the discharge hole 82 is situated precisely in the longitudinal axis of symmetry of the cartridge 8 and has a diameter of max. 0.1 mm. From the discharge hole the interior wall of the cartridge 8 passes on in an evolvent line and widens into the cylindrical section of the inside of the cartridge 8. Unlike the known earlier solutions, there is no need to apply alien materials like metal for the discharge hole 82, which, as extra material and producing cost, would dramatically raise the price of the cartridge 8. In the known earlier solutions it was impossible to generate a discharge hole of the required small diameter from the cartridge's own material, but especially not with ensuring the precise position and orientation. As the invented product, manufactured from die-cast plastic, proves, the task can be fulfilled successfully. In such a way a brand new, technically more advantageous and cheaper product is born as compared with known versions.

The patent description proves that this invention is a new, genuine solution, which entirely meets all the objectives. It perfectly follows the ideal process performed with manual injections with needles. Unlike earlier known devices with energy storage applying complex spring mechanisms, this solution safely separates the stage of punching the epidermis in the first moment from the moderate, seamless injection of the agent. All this is realized through a simple mechanism with reliable operation. Besides the device, the fitting agent cartridge is also a more practical, new solution. The uniform conical shape of the cartridge and the case ensures the precise, safe blocking of the two components through a simple concept. The discharge hole in the cartridge is die-cast from the cartridge's own material, which is extremely practical technically and financially, and, as an invention, it is completely new. The inventions summarized in the points of application each mean a significant progress in the field. Assembled, they are especially successful in supporting each other's advantages and achievements.

The invention claimed is:

1. A needleless injection device including a lower part receiving an agent cartridge and an upper part providing the energy needed for the injection, the upper part containing energy store units, including at least one start unit and at least one supplementary unit, capable of elastic form-change, the device further comprising:
    a lock mechanism maintaining tension of the energy store units and a release mechanism for releasing the lock mechanism;
    a tubular section of the lower part, provided with an external thread, extending into the upper part, the external thread coupling with an internal thread provided in the upper part, wherein the lower part is attached to the upper part in a revolving manner, and is movable telescopically within the upper part for producing a tension state of the energy store units; and
    a spacer moveable independently of the at least on supplementary unit within the upper part, the spacer maintaining a uniform longitudinal space between the at least one start unit and the lock mechanism from the time the tension state of the energy store units is produced until the lock mechanism is released,
    wherein:
        the at least one start unit is capable of storing 60-90% of the energy needed for total discharge when incurring a reversible elastic distortion of no more than 25% of an internal length of the agent cartridge; and wherein
        the at least one start unit includes a bundle of polyurethane springs fitted inside the device in a separate case; and
        upon release of the lock mechanism, the spacer transfers without impact the stored energy from the springs of the at least one start unit via the lock mechanism through a piston to contents of the agent cartridge, the stored energy being transferred without striking another body against the piston and with the cartridge and piston rod being in continuous contact during firing of the injection.

2. The device according to claim 1, wherein the supplementary units comprise one of
    (a) as few as 2 and as many as 8 volute springs fitted coaxially in each other and surrounding the axis of the upper part and
    (b) volute springs positioned symmetrically about the axis of the upper part.

3. The device according to claim 2, wherein the release mechanism comprises a release button situated at an upper end of the upper part and attached to a release rod that extends along the axis of the upper part to the lock mechanism.

4. The device according to claim 3, wherein a discharge hole of the agent cartridge is situated along the axis of symmetry of the agent cartridge.

5. The device according to claim 2, wherein a discharge hole in the agent cartridge is formed by an opening through the material of the agent cartridge.

6. The device according to claim 5, wherein the discharge hole of the agent cartridge is situated along the axis of symmetry of the agent cartridge.

7. The device according to claim 2, wherein a discharge hole of the agent cartridge is situated along the axis of symmetry of the agent cartridge.

8. The device according to claim 1, wherein the release mechanism comprises a release button situated at an upper end of the upper part and attached to a release rod that extends along the axis of the upper part to the lock mechanism.

9. The device according to claim 8, wherein a discharge hole in the agent cartridge is formed by an opening through the material of the agent cartridge.

10. The device according to claim 9, wherein the discharge hole of the agent cartridge is situated along the axis of symmetry of the agent cartridge.

11. The device according to claim 8, wherein a discharge hole of the agent cartridge is situated along the axis of symmetry of the agent cartridge.

12. The device according to claim 1, wherein a discharge hole in the agent cartridge is formed by an opening through the material of the agent cartridge.

13. The device according to claim 12, wherein the discharge hole of the agent cartridge is situated along the axis of symmetry of the agent cartridge.

14. The device according to claim 1, wherein a discharge hole of the agent cartridge is situated along the axis of symmetry of the agent cartridge.

* * * * *